(12) United States Patent
Ko et al.

(10) Patent No.: US 9,011,881 B2
(45) Date of Patent: Apr. 21, 2015

(54) PHARMACEUTICAL COMPOSITION FOR TREATING URINARY SYSTEM DISORDERS

(75) Inventors: Tse Hao Ko, Taichung (TW); Chen-Li Cheng, Taichung (TW); Ming-Chean Hung, Taichung (TW); Sheau-Yun Yuan, Taichung (TW); Shih I Chang, Taichung (TW)

(73) Assignee: Feng Chia University, Taichung (TW)

( * ) Notice: Subject to any disclaimer, the term of this patent is extended or adjusted under 35 U.S.C. 154(b) by 300 days.

(21) Appl. No.: 12/984,683

(22) Filed: Jan. 5, 2011

(65) Prior Publication Data

US 2012/0171250 A1    Jul. 5, 2012

(51) Int. Cl.
*A61K 9/00* (2006.01)
*A61K 9/14* (2006.01)
*A61K 33/44* (2006.01)

(52) U.S. Cl.
CPC .............. *A61K 33/44* (2013.01); *A61K 9/0034* (2013.01)

(58) Field of Classification Search
CPC ............................ A61K 9/0034; A61K 33/44
USPC .......... 424/400, 489, 125; 977/734, 742, 762, 977/215
See application file for complete search history.

(56) References Cited

U.S. PATENT DOCUMENTS

| | | | | |
|---|---|---|---|---|
| 5,616,222 A | * | 4/1997 | Maley et al. ................... | 204/294 |
| 2010/0278919 A1 | * | 11/2010 | Denes et al. ................... | 424/489 |
| 2011/0142946 A1 | * | 6/2011 | Tabata et al. ................... | 424/489 |
| 2012/0164429 A1 | * | 6/2012 | Shah et al. ................. | 428/293.1 |

OTHER PUBLICATIONS

Ormstad et al., ("Scanning electron microscopy of immunogold labeled cat allergens (Fe1 d 1) on the surface of airborne house dust particles" in Journal of Immunological Methods 187 (1995) 245-251).*

* cited by examiner

*Primary Examiner* — Blessing M Fubara
(74) *Attorney, Agent, or Firm* — Ming Chow; Sinorica, LLC (57) ABSTRACT

A pharmaceutical composition for treating urinary system disorders includes a carbon material carried by a water-containing carrier and having a carbon content over 60 percentage by weight (wt %), such that both of the carbon material and the water-containing carrier constitute a pharmaceutically acceptable water-containing carrier carrying the carbon material, and the carbon material falls within a range of 0.1 mg/ml to 500 mg/ml per unit dose and has a diameter from 2 nm to 2 mm, such that the pharmaceutical composition is capable of reducing symptoms of cystitis by contacting the carbon material with a bladder or related tissues of the bladder in an animal body.

15 Claims, 10 Drawing Sheets

| Content Test of Inflammation Inducer in Rat Urine | | | |
|---|---|---|---|
| Serial Number | First Urine Sample (EU/ml) | Second Urine Sample (EU/ml) | Third Urine Sample (mg) |
| M1-1(Normal) | - | 1.0 | 112 |
| M1-2(LPS) | 9.6 | 1.8 | 177.3 |
| M1-3(LPS-ACF) | 36.6 | 1.0 | 134.8 |

| Concentration of PCT in Rat Serum and Weight of Bladder | | |
|---|---|---|
| Serial Number | PCT Concentration (ng/ml) | Weight of Bladder (mg) |
| M1-1(Normal) | 0.021 | 109.8 |
| M1-2(LPS) | 0.036 | 177.6 |
| M1-3(LPS-ACF) | <0.02 | 138.1 |

PHARMACEUTICAL COMPOSITION FOR TREATING URINARY SYSTEM DISORDERS

BACKGROUND OF THE INVENTION

1. Field of the Invention

The present invention relates to a pharmaceutical composition, and more particularly to a pharmaceutical composition includes a water-containing carrier carrying a carbon material, such that both water-containing carrier and carbon material constitute a pharmaceutically acceptable water-containing carrier carrying the carbon material for treating urinary system disorders.

2. Description of the Prior Art

Urinary tract infection (UTI) is inevitable in patients received prolonged indwelling urinary catheter and the use of catheters that can result in the introduction of bacteria into the urinary bladder. The indications of application of urinary catheterization include bladder outlet obstruction (BOO), either functional BOO, such as spinal cord injury or organic BOO, such as prostatic hypertrophy or urethral stricture, when accurate output monitoring is required, for selected operation in the perioperative period, to assist in healing of pressure ulcer. The indwelling catheter impairs host defences by providing access of microorganisms to the bladder. A variety of infecting organisms involved in catheter-related UTI. *Escherichia coli* is the most common, and other important organisms are *Enterobacter* spp., *Pseudomonas aeruginosa, Klebsiella* spp., *Serratia* spp., and *Candida* spp.

The presence of bacteriuria with $10^5$ or more colony forming units per ml (CFU/ml) is the simplest way of diagnosing the cystitis, Therefore, a large quantity of bacteria in urine indicates the occurrence of cystitis or pyelonephritis. From statistics of nosocomial infections occurred in intensive care units in Taiwan in 2007, it is found that the urinary tract infection occupies 37.5% of the total number of nosocomial infections and ranks No. 1 among all kinds of nosocomial infections in Taiwan, regardless of its occurrence in medical centers or regional hospitals. At present, the urinary system disease caused by bacterial infections in different age groups still rank the highest among urinary tract infections. In addition, an invasive treatment such as catheter insertion and cystoscopic examination is the most common treatment adopted by hospitals, and such treatment may be one of the main causes of exogenous infections, since bacteria are introduced into a bladder while there is a risk of causing an ascending bacterial infection that results in a bacterial cystitis, or even worse an acute cystitis or nephritis. In the most common bacterial cystitis, redness, swelling and vascular congestion occur at the position of the inflammation. If cystitis occurs and causes discomfort and pain to the bladder and urgent micturition and related symptoms, and the cystitis is treated improperly, a severe infection may occur at the bladder or incur a failure of a patient's kidney that requires dialysis later, or will even incur a risk of fatal sepsis/urosepsis.

At present, the initiasl therapy of patients with catheter-acquired UTI is whether oral or parenteral antibiotics. Parenteral therapy is indicated in patients with severe toxic signs, including high fever, unstable vital signs oror patients who cant not tolerate oral administration. Intravesical instillation of antibiotics is an alternative approach in treatment of chronic inwelling catheter induced UTI, especially fungal urinary tract infection. The antimicrobial should be prescribed based on the urine culture results. A variecty of antimicrobial agents are used for treatment of catheter-related UTI, including penicillins, cephalosporines, fluoroquinolones, aminoglycosides, . . . etc. The techniques used for preventing a bacterial infection of an urinary tract include antibiotic methods, and application of coating medicine on the surface of a catheter, and using silver or silver plated catheters, etc. Recurrent UTI required multiple coursed of antibiotice therapy, thus increasing the probability of development of drug-resistant bacteria.

Although a large quantity of bacteria will be killed after taking the aforementioned medication treatments, the medication treatments also cause the production of lipopolysaccharides (LPS), and the LPS comes from the cell walls of bacteria and induces inflammatory reaction. Bladder cells to secrete cytokine including IL-1 $\alpha$, $\beta$, TNF-$\alpha$, IL-6, IL-8 and IL-10 inflammatory factors, and such inflammatory factors play an important role for the white blood cell accumulation of a bladder and cause the characteristics of inflammation including redness, swelling, heat and pain, or even internal bleeding in a severe inflammation. The aforementioned phenomenon usually occurs in patients wearing a catheter regularly since exogenous bacterial infections causing complicated infections such as chronic cystitis are inevitable, and some patients may be attacked by severe bacterial infections or even fatal sepsis/urosepsis due to incomplete treatments. Furthermore, the treatments of cystitis or the techniques of preventing bacterial infections of urinary tracts seldom release the symptom continuously and may cause side effects in a long-term treatment and an application of the prevention techniques.

SUMMARY OF THE INVENTION

Therefore, it is a primary objective of the invention to provide an effective cystitis treatment, as a cystitis treatment usually relies on an antibacterial medication for the treatment of an infection and fails to achieve the expected effect, and patients usually delay the time of treatments after they are infected by bacteria and a large quantity of bacteria have been reproduced, and visit a doctor until the symptoms including redness, swelling, heat and pain occur, which create a larger burden to the patient and incurs a higher risk of a drug resistance of bacteria, and these are the main causes for the difficulty of curing complicated bacterial infections or drug-resisting bacterial cystitis, and repairing the mucosa and lamina propria tissues of the bladder in order to prevent further bacterial invasions. Therefore, it is necessary to eliminate the bacteria of a cystitis and the toxic matters in the patient's body quickly, repair damaged mucosa and lamina propria tissues to prevent further invasions and reproductions of the bacteria, and promote the healing of wounds at the surface of the bladder before the infection or its recurrence can be controlled effectively, so as to release the symptoms of cystitis.

To achieve the foregoing objective, the present invention adopts the following technical measures and provides a pharmaceutical composition for treating urinary system disorders, and the pharmaceutical composition comprises a carbon material carried by a water-containing carrier and having a carbon content over 60 percentage by weight (wt %), such that both of the water-containing carrier and the carbon material constitute a pharmaceutically acceptable water-containing carrier carrying the carbon material, and the water-containing carrier carries a carbon material ranging from 0.1 mg/ml to 100 mg/ml per unit dose, and the carbon material has a diameter ranging from 2 nm to 2 mm and a carbon layer stack thickness (Lc) ranging from 1 nm to 1000 mm. The carbon material further comprises a metal particle selected from the collection of silver, platinum, palladium, gold, zinc and copper particles and any combination of the above, and the metal particle has a diameter falling within a range from 2 nm to 2 mm.

The present invention further provides a pharmaceutical composition for treating urinary system disorders, and the pharmaceutical composition comprises a carbon material or a carbon material combined with metal particles and contacted with a bladder and related tissues of the bladder in an animal body, wherein a carbon material composed of active carbon can be used for adsorbing bacteria, and the low-concentration ions of a uniformly distributed fine granular metal can be used for the disinfection effect and produce an effect of quickly adsorbing bacteria and the endotoxin which is the lipopolysaccharides (LPS) produced by the cell walls of dead bacteria. Clinically, the endotoxin (LPS) will induce bladder cells to secrete cytokine including IL-1 $\alpha$, $\beta$, TNF-$\alpha$, IL-6, IL-8 and IL-10 inflammatory factors, and such inflammatory factors play an important role of causing a white blood cell accumulation to the bladder, and characteristics of inflammation such as redness, swelling, heat and pain. The invention has the effects of reducing the endotoxins that causes the inflammation and reducing the symptoms of cystitis, while controlling infections effectively, preventing the recurrence of the cystitis, promoting the healing of wounds at the surface of the bladder, releasing the symptoms of cystitis, and treating and preventing cystitis, acute cystitis, chronic cystitis, hemorrhagic cystitis, bacterial cystitis, emphysematous cystitis, and interstitial cystitis, or curing patients with wounds in their bladder or urinary tract or patients with a urinary tract infection. The invention can also achieve the effects of controlling infections, preventing the recurrence of cystitis, promoting the healing of wounds at the surface of a bladder, and releasing the symptoms of cystitis effectively.

DETAILED DESCRIPTION OF THE PREFERRED EMBODIMENTS

A pharmaceutical composition for treating urinary system disorders in accordance with a preferred embodiment of the present invention comprises a water-containing carrier for carrying a carbon material having a carbon content with a percentage by weight of over 60 wt %, such that the water-containing carrier and the carbon material form a pharmaceutically acceptable water-containing carrier carrying the carbon material, wherein the carbon material is one selected from the collection of free carbon fiber, active carbon fiber, active carbon, graphite, expanded graphite, nano-carbon tube, carbon nanocapsule, coke ball and carbon black, or a combination of the above, and the carbon material has a diameter falling within a range from 20 nm to 2 mm, a carbon layer stack thickness (Lc) falling within a range from 1 nm to 1000 mm, and a structure and specific surface area (BET) from 20 $m^2/g$ to 4000 $m^2/g$, wherein the carbon material of a preferred embodiment of the present invention is active carbon fiber powder or active carbon, and the carbon content has a percentage by weight over 80 wt %, a structure and specific surface area (BET) from 200 $m^2/g$ to 3000 $m^2/g$. In the meantime, the water-containing carrier is one selected from the collection of free buffer solution, antibiotic medicament, cystitis medication, and any combination of the above, and the water-containing carrier carries over 0.01 mg/ml of the carbon material per unit dose, wherein the water-containing carrier carries 0.1 mg/ml to 500 mg/ml of the carbon material per unit dose in accordance with a first preferred embodiment of the present invention preferred embodiment. The composition and effects of the second preferred embodiment of present invention are the same as those of the first preferred embodiment, and thus will not be described here again. The carbon material of the second preferred embodiment further comprises a metal particle and the metal particle is a fine granular metal particle selected from free silver, platinum, palladium, gold, zinc and copper particles or a combination of the above, and the metal particle has a diameter ranging from 2 nm to 2 mm and occupies a percentage by weight of the carbon material less than 20 wt %. In the second preferred embodiment, the fine granular metal occupies a percentage by weight of the carbon material below 5 wt %. The fine granular metal and the carbon material are combined and carried by the water-containing carrier to form the pharmaceutical composition for treating urinary system disorders.

The antibiotic medicament of the water-containing carrier is one selected from the collection of free trimethoprim-sulfame-thoxazole (TMP-SMX), trimethoprim (TMP), sulfame-thoxazole (SMX), fluoroquinolones, ciprofloxacin, ofloxacin, cephalexin and tetracycline or a combination of the above, and the cystitis medication of the water-containing carrier is one selected from the collection of free dimethyl sulfoxide, clorpactin, heparin, hyaluronic acid (HA), adriamycin (ADM), chondroitin sulfate, sodium bicarbonate, silver nitrite, pentosan polysulfate sodium, cromolyn sodium, pencillin, nitrofurazone, gentamicin and mild silver protein, or a combination of the above.

The carbon material of the pharmaceutical composition or the carbon material combined with the metal particle can be contacted with a bladder and its related tissues in an animal body for treating and preventing cystitis, acute cystitis, chronic cystitis, hemorrhagic cystitis, bacterial cystitis, emphysematous cystitis, interstitial cystitis, bladder or urinary tract to cure patients with wounds and urinary tract infections, while controlling the infections effectively, preventing the recurrence of cystitis, promoting the healing of wounds at the surface of a bladder, and releasing the symptoms of cystitis.

The structure, characteristics, technical measures and expected effects of the present invention will become apparent with the detailed description of preferred embodiments accompanied with related drawings as follows.

With reference to FIGS. 1 to 5, the carbon material of the pharmaceutical composition is an active carbon fiber, preferably the active carbon fiber produced and sold by TAIWAN CARBON TECHNOLOGY CO., LTD, and grounded into particles of with a diameter from 50 μm to 100 μm, and the structure and specific surface area (BET) of the carbon material is 200 $m^2/g$~2000 $m^2/g$, and the water-containing carrier of this preferred embodiment of the present invention is a buffer solution, and the buffer solution is preferably a sterile water, wherein the carbon material is added into the buffer solution and mixed thoroughly to form the water-containing carrier carrying the carbon material, and the water-containing carrier carries 0.2 mg/ml of the carbon material per unit dose, and three female Sprague-Dawley rats are used, and the weight of each rat is approximately 290 g, and the rats are divided into the following groups:

1. M1-1 (Normal): This group consists of normal rats without having the injection of an inflammation inducer or the induction of cystitis.
2. M1-2 (LPS): This group consists of rats injected with an inflammation inducer to induce cystitis.
3. M1-3 (LPS-ACF): This group consists of rats injected with an inflammation inducer to induce cystitis, and the water-containing carrier together with the carbon material is injected into a patient's bladder for the medical treatment.

Before experiments start, the rats are paralyzed by urethane first, and then the paralyzed rats are confirmed and fixed onto a soft board by tapes, and a polyethylene tube (PE-50) is used for the catheter insertion of the urinary tract. The following steps are carried out after the foregoing procedure completes.

Two rats are selected from the M1-2 (LPS) group and the M1-3 (LPS-ACF) group respectively and protamine sulfate (PS) is injected from the urinary tract into the bladder of the rats. The bladder mucosa of the bladder of the two rats from the M1-2 (LPS) group and the M1-3 (LPS-ACF) group are injured, and then an inflammation inducer is injected, wherein the injected inflammation inducer of this preferred embodiment of the present invention is an endotoxin such as the lipopolysaccharides (LPS) used for inducing the inflammation of the injured bladder and causing the rat bladder to have an inflammation. Normal saline is injected to rinse the bladder in 45 minutes after the protamine sulfate (PS) is injected, so as to control the range of injury and prevent the protamine sulfate (PS) from further harming lamina propria cells of the bladder.

After the bladder is rinsed, a quantity of 750 E.U. of the inflammation inducer which is the endotoxin is injected to induce the bladders of the rats to have the inflammation again. In the meantime, the inflammation inducer is injected once every half hour for a total of two times, and then normal saline is used for rinsing the bladder, and first urine samples of the three rats are collected respectively after an hour.

The pharmaceutical composition is injected into the M1-3 (LPS-ACF) group of rats, and the pharmaceutical composition containing the water-containing carrier together with the carbon material is added into a buffer solution, and whose concentration per unit dose is 4 mg/20 ml, and only the rats of the M1-2 (LPS) group are injected with normal saline, and the injection takes place once every half an hour for a total of four injections. After an hour, second urine samples of the three rats are collected respectively. After a total of 24 hours, the bladders of the three rats are collected and weighted, and H & E stained pathogenic slides of the bladders of the rats from the three groups are prepared.

Figure 1:
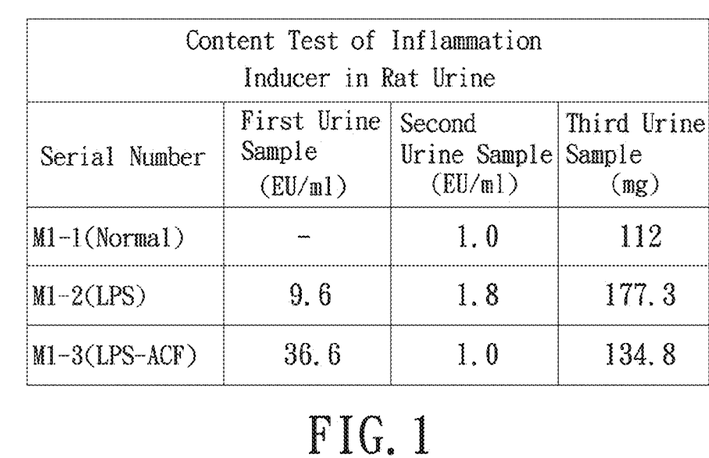
FIG. 1 shows a table comparing the content of the inflammation inducer in a test and the weight of bladders from different groups of rat urine samples in accordance with a first preferred embodiment of the present invention.

In FIG. 1, the M1-1 (Normal) group is a control which is not adopted in the analysis of the first urine samples, and the inflammation inducer used for the rats of the M1-2 (LPS) group has a concentration up to 9.6 EU/ml, the inflammation inducer used for the rats of the M1-3 (LPS-ACF) has a concentration up to 36.0 EU/ml. After three hours, a second analysis takes place for the collected urine samples, and the M1-1 (Normal) group is a control, whose inflammation inducer has a content of 1.0 EU/ml, and the content of the inflammation inducer for the M1-2 (LPS) group is dropped to 1.8 EU/ml. After the pharmaceutical composition containing the water-containing carrier together with the carbon material is injected to the group M1-3 (LPS-ACF), the content of the inflammation inducer will drop to 1.0 EU/ml. In the comparison of the contents of the inflammation inducers used in the three rats from the M1-1 (Normal) group, the M1-2 (LPS) group and the M1-3 (LPS-ACF) group, the results of the M1-3 (LPS-ACF) group and the M1-2 (LPS) group injected with the inflammation inducer show that the inflammation inducer content of in the first urine sample is 9.6 EU/ml, and the inflammation inducer goes through the metabolism held in the rat bodies, a content of 1.8 EU/ml of the inflammation inducer remains in the second urine in the rat bodies after three hours. The concentration of the inflammation inducer of the rat of the M1-3 (LPS-ACF) injected with the inflammation inducer to induce cystitis is up to 36.0 EU/ml in the first urine sample, but after the pharmaceutical composition containing the water-containing carrier together with the carbon material is injected, the content of the inflammation inducer in the second urine sample drops to 1.0 EU/ml, which equals to the content of the inflammation inducer of the M1-1 (Normal) control group and indicates that the pharmaceutical composition of the water-containing carrier carrying the carbon material has produced a treatment effect to the inflamed rat bladder.

In FIG. 1, the weight of bladders of the three rats also shows the treatment effect of the injection of the pharmaceutical composition with the water-containing carrier carrying the carbon material, wherein the weight of the rat bladder of the M1-2 (LPS) group is 177.3 mg; the weight of the rat bladder of the M1-3 (LPS-ACF) group drops to 134.8 mg after the inflammation inducer is injected to induce cystitis and the pharmaceutical composition containing the water-containing carrier together with the carbon material is injected for the treatment, and it shows that the pharmaceutical composition has produce a treatment effect of curing the edema caused by the cystitis.

Figure 2:
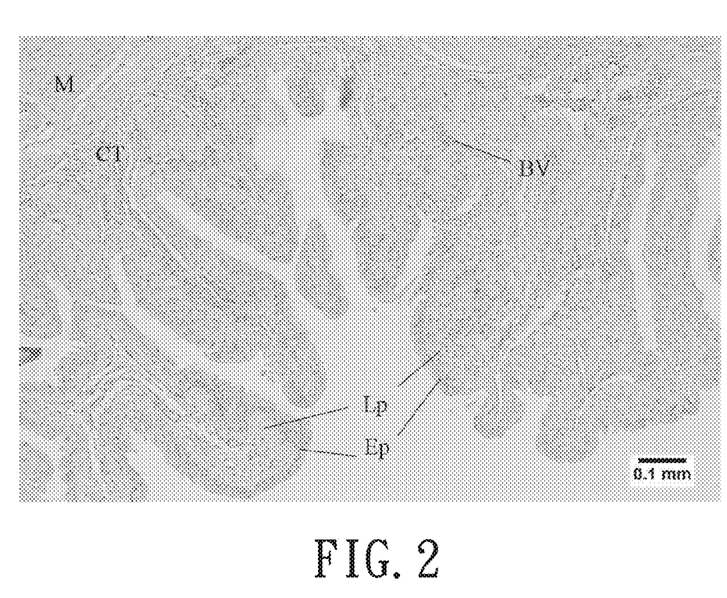
FIG. 2 shows a H & E stained slice of a bladder selected from the M1-1 (Normal) group of rats including Blood Vessel (BV), Epithelium (Ep) that constitutes mucosal epithelial cells, Muscle (M), Connective Tissue (CT) and lamina propria (Lp) in accordance with a first preferred embodiment of the present invention.
Figure 3:
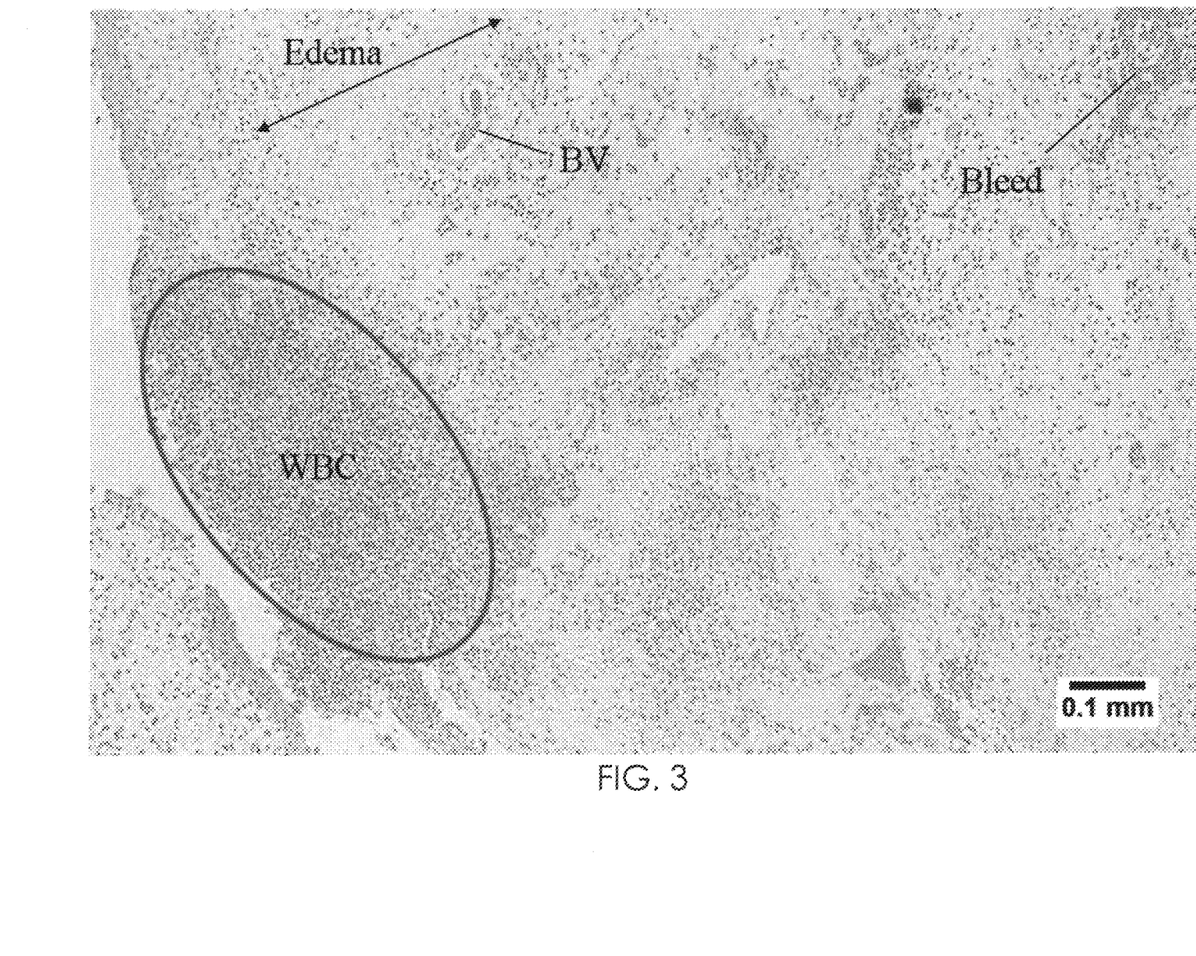
FIG. 3 shows a H & E stained slice of a bladder selected from the group of inflamed M1-2 (LPS) rats induced by an inflammation inducer and having white blood cell (WBC) accumulation, edema and bleeding occurred at the surface of the inflamed bladder in accordance with a first preferred embodiment of the present invention.
Figure 4:
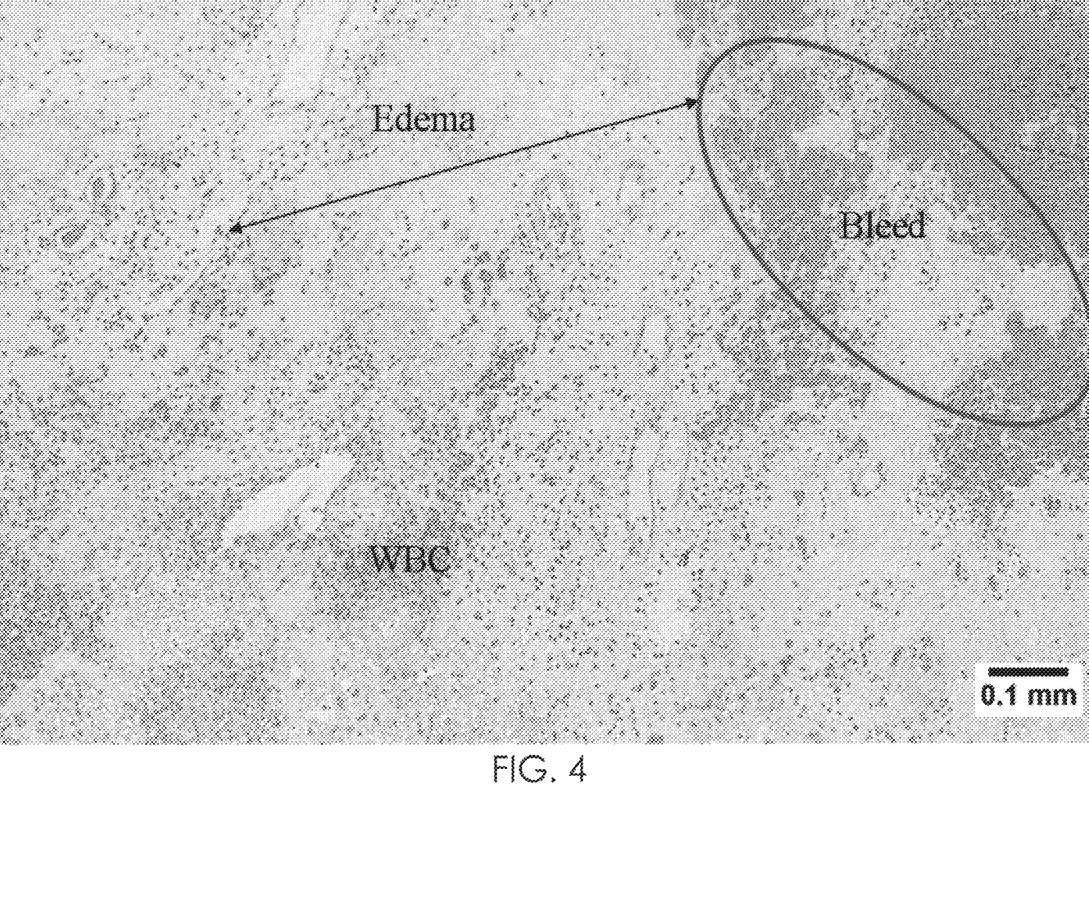
FIG. 4 shows a H & E stained slice of tissues under a bladder mucosa of a bladder selected from the group of M1-2 (LPS) rats and having a severe internal bleeding in accordance with a first preferred embodiment of the present invention.
Figure 5:
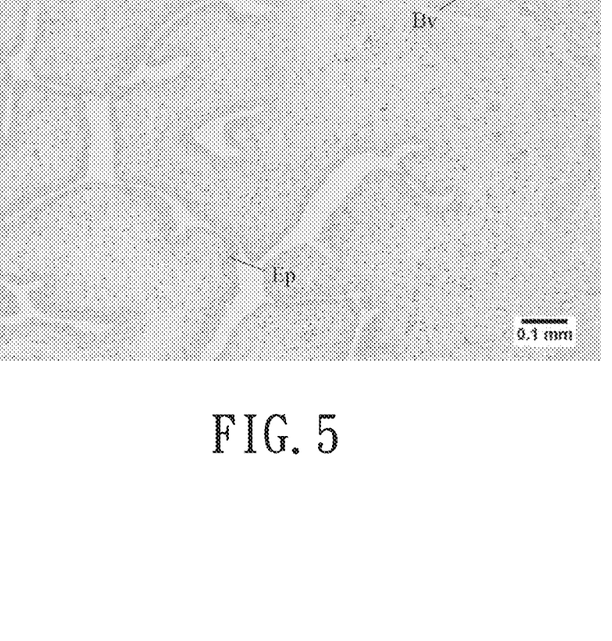
FIG. 5 shows a H & E stained slice of an inflamed bladder selected from the group of M1-3 (LSP-ACF) rats and induced by a cystitis inducer, after a treatment of injecting a pharmaceutical composition containing a carbon material carried by a water-containing carrier in accordance with a first preferred embodiment of the present invention.

With reference to FIG. 2 for a H & E stained slice of a bladder of a rat selected from the M1-1 (Normal) group for a further understanding of the condition inside the rat bladder, FIG. 2 clearly shows the normal condition, and smooth bladder mucosa and epithelial cells on the surface of the bladder are observed. With reference to FIG. 3 for a H & E stained slice of an inflamed bladder of a rat selected from the M1-2 (LPS) group and induced by the inflammation inducer, a white blood cell accumulation occurred at the lamina propria of the bladder under the mucosa due to the inflammation of the rat selected from the M1-2 (LPS) group can be observed. In FIG. 4, a severe internal bleeding occurred at the internal tissues of the rat selected from the M1-2 (LPS) can be observed. With reference to FIG. 5, the rat selected from the M1-3 (LPS-ACF) is inflamed by an endotoxin which is the inflammation inducer, and injected with the pharmaceutical composition containing the water-containing carrier together with the carbon material for the treatment, and the H & E stained slices of the bladders are used for comparing the mucosa tissue of the bladder of the M1-3 (LPS-ACF) group with the M1-1 (Normal) group as shown in FIG. 2, and the bladders of both groups show normal mucosa tissues, and no characteristics of inflammation including white blood cell accumulation, edema, and internal bleeding are found in the rat of the M1-3 (LPS-ACF) group, and thus it shows that the pharmaceutical composition containing the water-containing carrier together with the carbon material has produced the treatment effect to the inflamed bladder of the rat.

With reference to FIGS. 6 to 9, this preferred embodiment is substantially the same as the first preferred embodiment of the present invention, and thus will not be described here again, but this preferred embodiment measures the content of the procalcitonin (PCT) in the rat serum, and the concentration of the procalcitonin in the rat serum is an important index for determining a severe bacterial infection and a generalized inflammation, so that if the concentration of the procalcitonin rises, it shows that the cystitis is a bacterial infection, a sepsis/urosepsis shock or other severe generalized bacterial infections.

Figure 6:
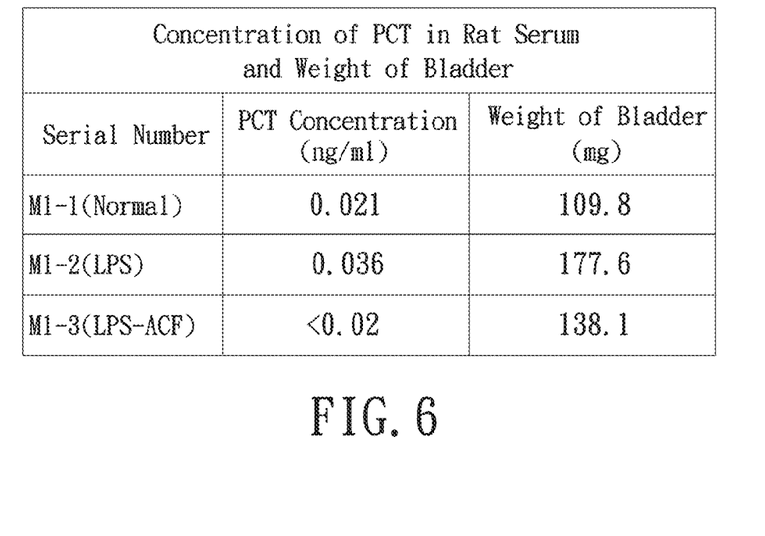
FIG. 6 shows a table comparing the concentration of pro-calcitonin (PCT) in rat serum and the weight of a bladder selected from different groups of rats in accordance with a first preferred embodiment of the present invention.

In FIG. 6, the M2-1 (Normal) group is a control of normal rats, whose concentration of procalcitonin is 0.021 ng/ml, and the M2-2 (LPS) group of inflamed rats are induced by the inflammation inducer, and whose concentration of procalcitonin is increased to 0.036 ng/ml, and the M2-3 (LPS-ACF) group of inflamed rats are induced by the inflammation inducer and injected with the pharmaceutical composition of the invention has a concentration of procalcitonin of 0.02 ng/ml. The comparison shows that the concentrations of procalcitonin in the rats of the M2-3 (LPS-ACF) group and the M2-1 (Normal) group are substantially the same. In the meantime, the weight of bladder of the rat of the M2-2 (LPS) group is 177.6 mg, and the weight of the bladder of the rat of M2-3 (LPS-ACF) after the treatment drops to 138.1 mg. Obviously, the pharmaceutical composition containing the water-containing carrier together with the carbon material has a treatment effect to cystitis.

Figure 7:
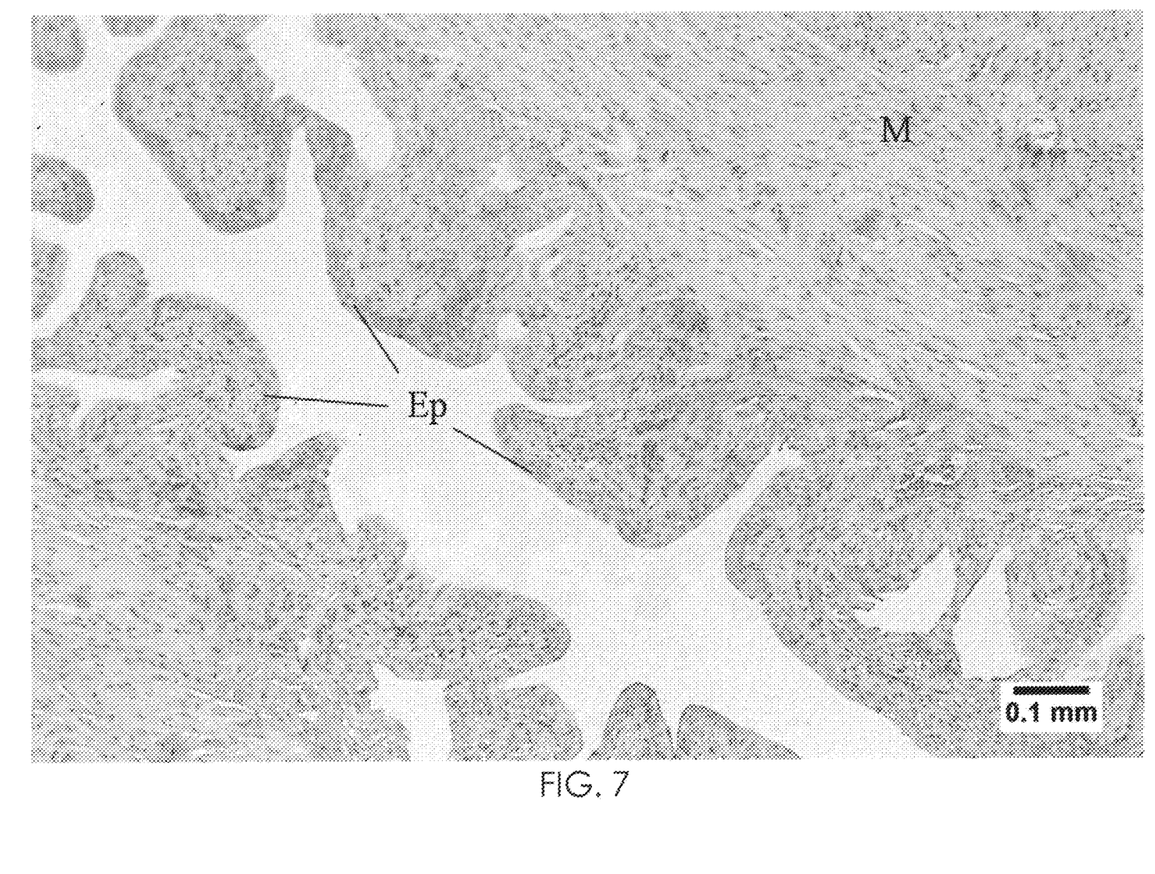
FIG. 7 shows a H & E stained slice of a bladder selected from the group of M2-1 (Normal) rats in accordance with a first preferred embodiment of the present invention.
Figure 8:
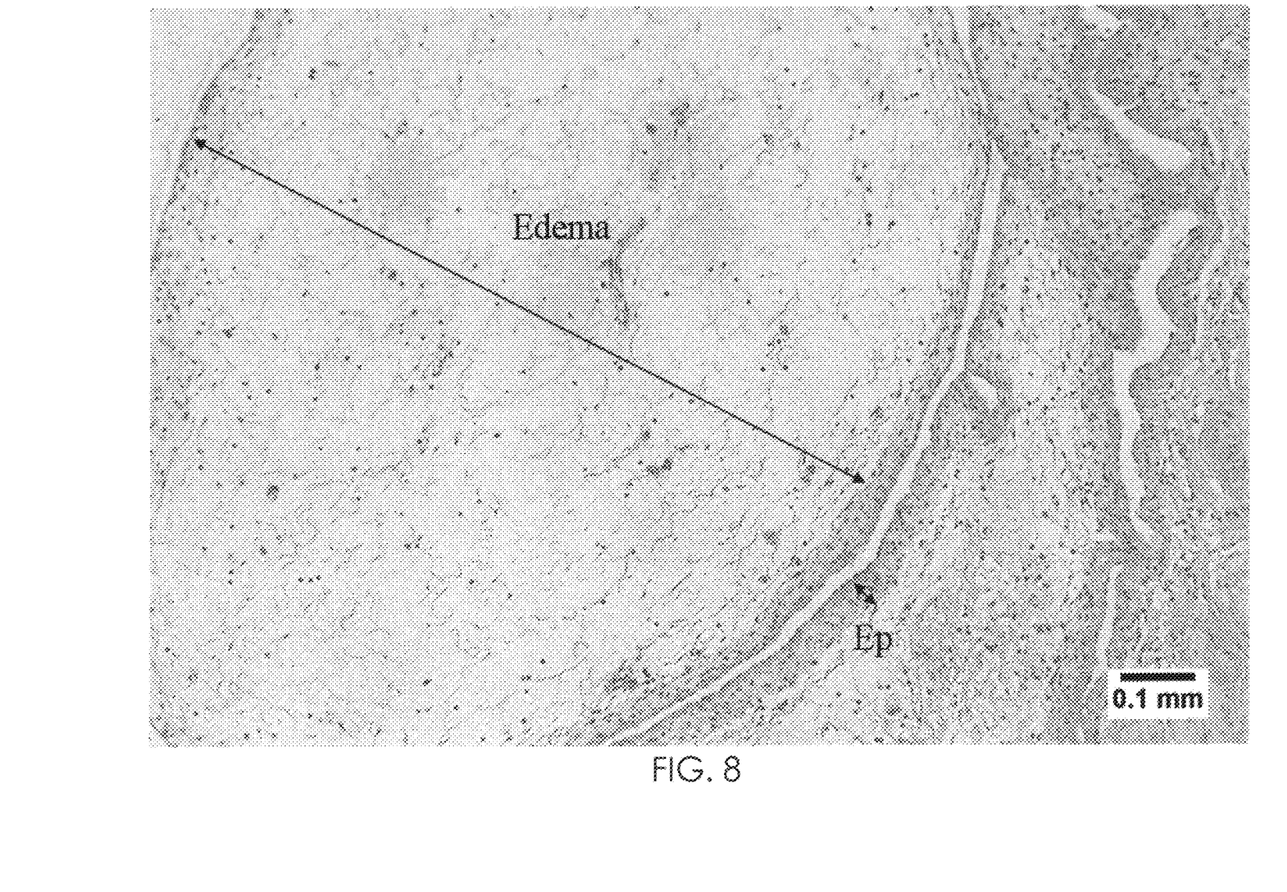
FIG. 8 shows a H & E stained slice of an inflamed bladders selected from the M2-2 (LPS) group and induced by a cystitis inducer in accordance with a first preferred embodiment of the present invention, and the left side of the figure indicates the occurrence of an extremely severe edema.
Figure 9:
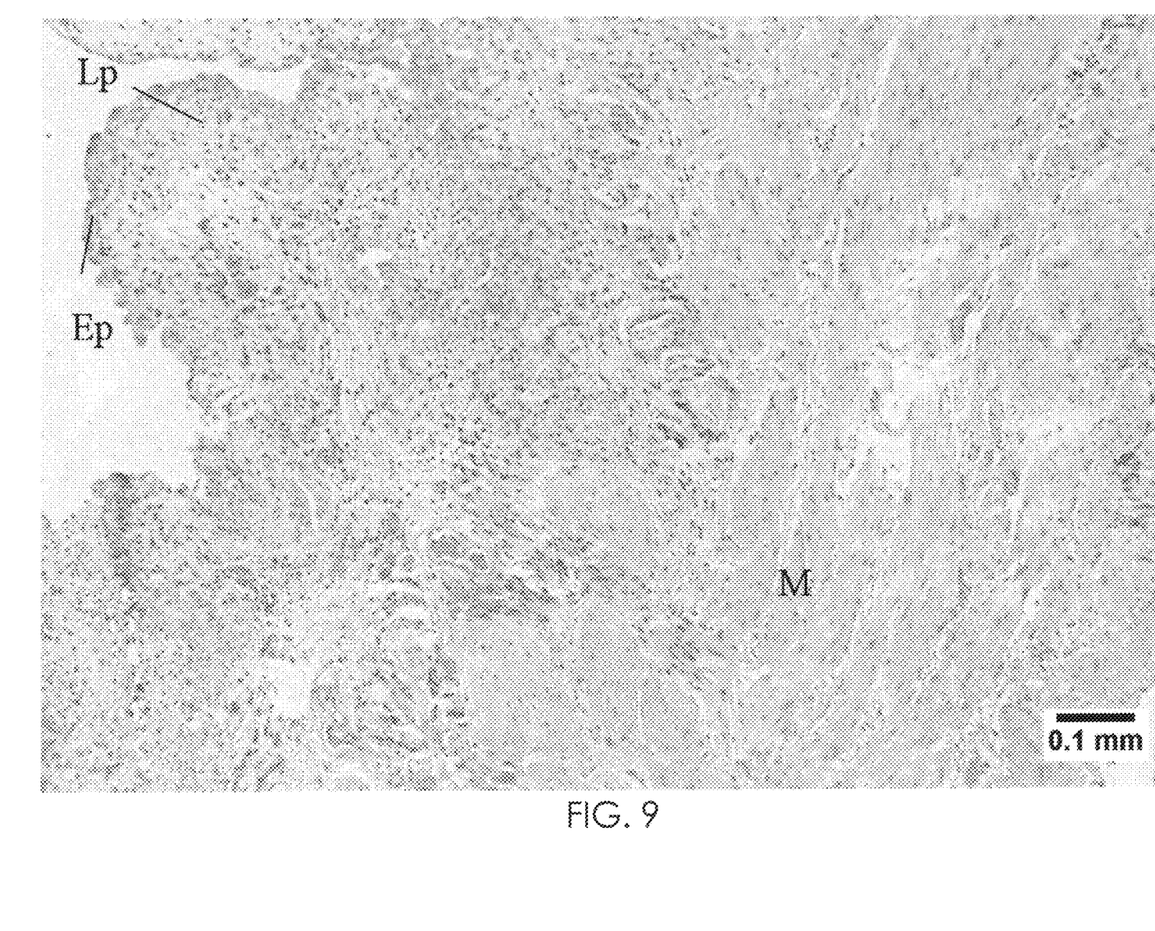
FIG. 9 shows a H & E stained slice of an inflamed bladder selected from the M2-3 (LPS-ACF) group and induced by a cystitis inducer after a treatment of injecting a pharmaceutical composition of a carbon material carried by a water-containing carrier in accordance with a first preferred embodiment of the present invention.

In FIGS. 7 to 9 for H & E stained pathological tissue slices of bladders of rats from different groups respectively, the slide of the bladder tissue of the rat of the M2-1 (Normal) group as shown in FIG. 7 shows a smooth bladder mucosa, and the slide of the bladder tissue of the rat of the M2-2 (LPS) group as shown in FIG. 8 show a severe edema on the left side of the figure, and the slide of the bladder tissue of the rat of the M2-3 (LPS-ACF) group as shown in FIG. 9 shows a smooth surface of the bladder mucosa and no severe inflammation symptom including white blood cell accumulation, edema and internal bleeding. It shows that the pharmaceutical composition containing the water-containing carrier together with the carbon material has produced a treatment effect to the inflamed bladder.

Figure 10:
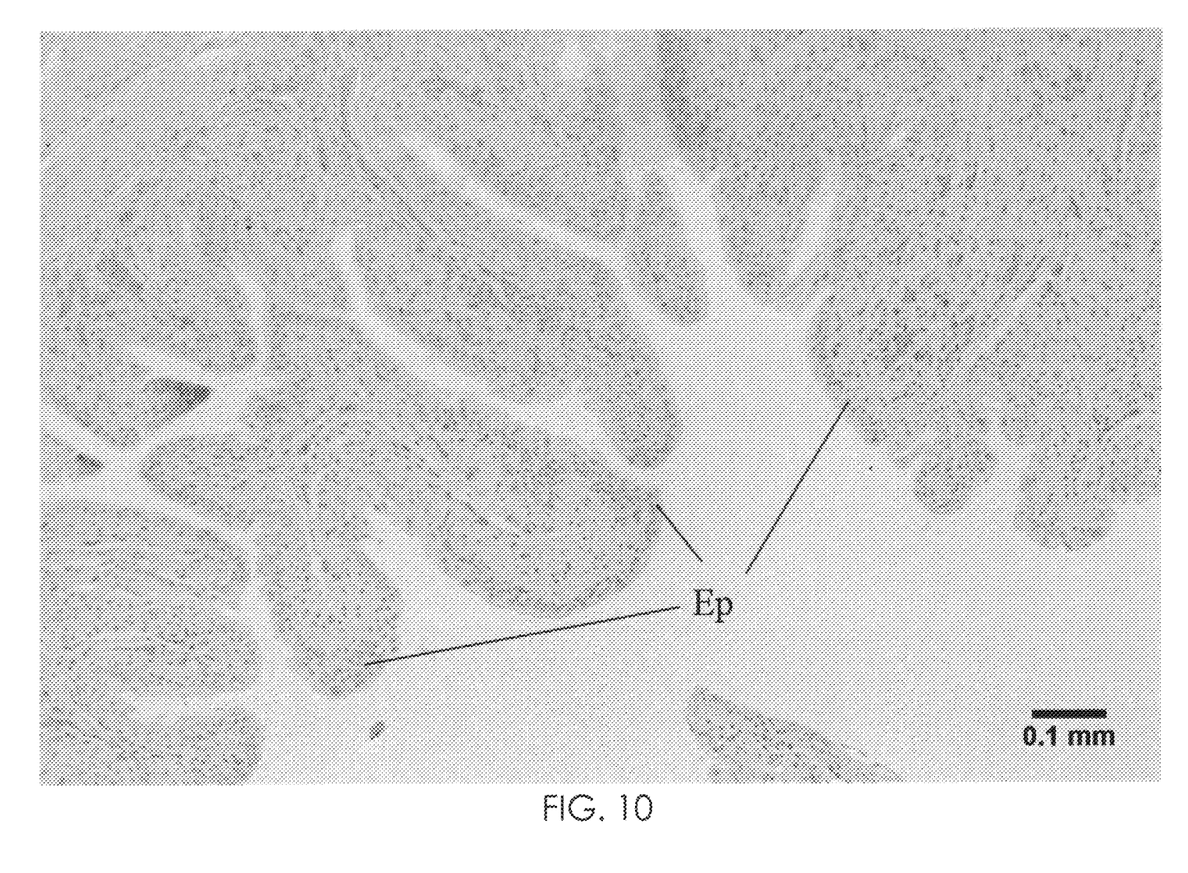
FIG. 10 shows a H & E stained slice of a bladder selected from the M3-1 (Normal) group in accordance with a second preferred embodiment of the present invention.
Figure 11:
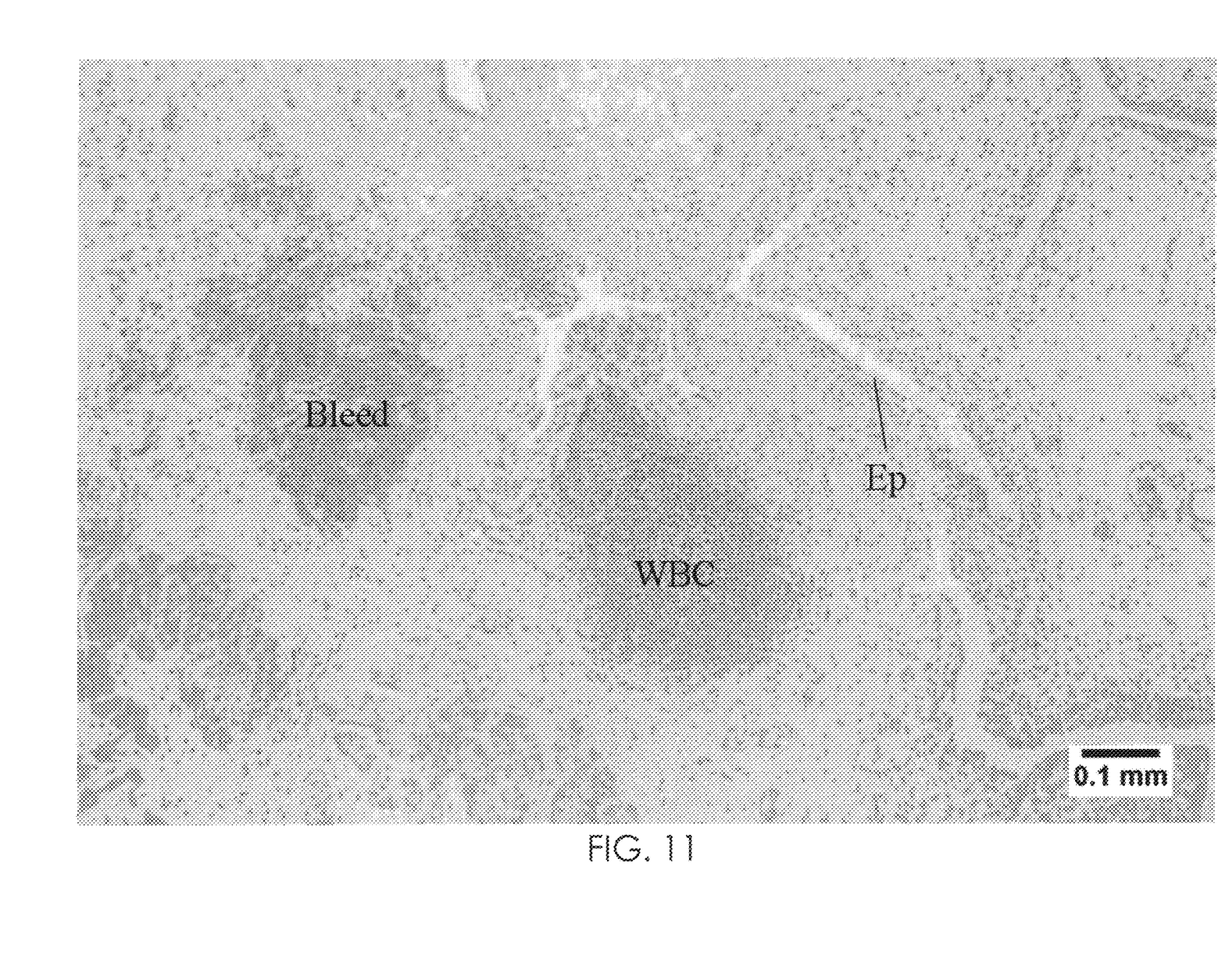
FIG. 11 shows a H & E stained slice of an inflamed bladder selected from the M3-2 (LPS) group and induced by a cystitis inducer in accordance with a second preferred embodiment of the present invention, and the left side of the figure indicates the occurrence of a white blood cell accumulation and an internal bleeding.
Figure 12:
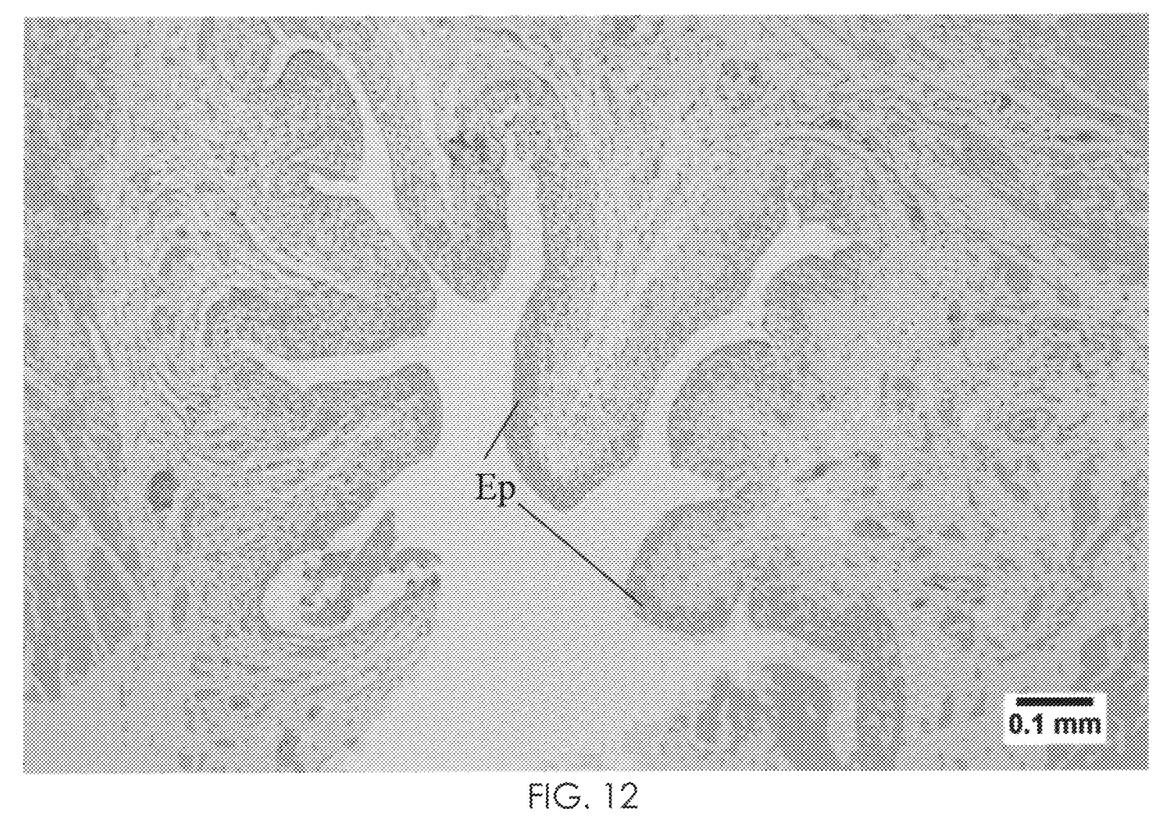
FIG. 12 shows a H & E stained slice of an inflamed bladder selected from the M4-3 (LPS-ACF) group and induced by a cystitis inducer after a treatment of injecting a pharmaceutical composition of a carbon material carried by a water-containing carrier in accordance with a second preferred embodiment of the present invention.

With reference to FIGS. 10 to 12 for H & E stained pathological tissue slices of rat bladders of different groups respectively, this preferred embodiment is substantially the same as the first preferred embodiment of the present invention, and thus will not be described here again, but the pharmaceutical composition injected to the rat of the M3-3 (LPS-ACF) for treating cystitis in accordance with a second preferred embodiment of the present invention includes a metal particle combined with the carbon material and carried by the water-containing carrier to produce the pharmaceutical composition, and the metal particle of the second preferred embodiment is a nanoscale sliver particle. With reference to FIG. 10 for a H & E stained slice of a normal rat bladder of the M3-1 (Normal) group, no inflammation, edema or internal bleeding is found. With reference to FIG. 11 for an inflamed bladder of the rat of the M3-2 (LPS) group and induced by the inflammation inducer, no characteristics of severe inflammation including white blood cell accumulation, edema and internal bleeding are found. In FIG. 12, the rat of the M4-3 (LPS-ACF) induced by the inflammation inducer and injected with the carbon material containing silver particles for the treatment, no characteristics of severe inflammation including white blood cell accumulation, edema and internal bleeding are found. Therefore the pharmaceutical composition produced by combining the carbon material and the silver particles has the disinfection effect and reducing the symptoms of cystitis.

In summation of the description above, the present invention has the following advantages and effects:

1. The pharmaceutical composition for treating urinary system disorders in accordance with the present invention includes a carbon material carried by a water-containing carrier, such that both of the carbon material and the water-containing carrier constitute a pharmaceutically acceptable water-containing carrier carrying the carbon material, which is acceptable to a bladder mucosa to release the symptoms of cystitis and provide a long-time treatment effect.

2. The pharmaceutical composition for treating urinary system disorders in accordance with includes a carbon material carried by a water-containing carrier, such that both of the carbon material and the water-containing carrier constitute a pharmaceutically acceptable water-containing carrier carrying the carbon material for repairing the bladder mucosa to achieve the effect of further treatments.

3. The pharmaceutical composition for treating urinary system disorders in accordance with includes a carbon material having a metal particle selected from the collection of free silver, platinum, palladium, gold, zinc, copper, and a combination of the above, and the metal particle has a diameter from 2 nm to 2 mm, such that the carbon material combined with nanoscale metal particles can enhance the disinfection effect and reduce the symptoms of cystitis.

4. The pharmaceutical composition for treating urinary system disorders in accordance with includes a carbon material having a higher structure and specific surface area (BET), a good biological compatibility, and a capability of adsorbing bacteria actively to reduce the quantity of pathogenic bacteria below $10^5$ CFU quickly, and adsorbing exotoxins and endotoxins (LPS) of the bacteria to retard the inflammation action of cystitis, and discharging the LPS together with urine out of the patient's body to achieve the expected effects.

In summation of the description above, the present invention improves over the prior art and complies with patent application requirements, and thus is filed for patent application.

While the invention has been described by device of specific embodiments, numerous modifications and variations could be made thereto by those generally skilled in the art without departing from the scope and spirit of the invention set forth in the claims.

What is claimed is:

1. A pharmaceutical composition for treating urinary system disorders, comprising a carbon material and a water-containing carrier;
    the carbon material being carried by the water-containing carrier;
    the pharmaceutical composition having a carbon content greater than 60% by element weight;
    both of the carbon material and the water-containing carrier constitute a pharmaceutically acceptable water-containing carrier carrying the carbon material; the carbon material having a diameter falling within a range from 2 nm to 2 mm;
    wherein the carbon material has a carbon layer stack thickness (Lc) falling within a range from 1 nm to 1000 mm;
    the carbon material is one selected from the group consisting of carbon fiber, active carbon fiber, active carbon, nano-carbon tube,
    carbon nanocapsule, coke ball, carbon black, and a combination of the above;
    wherein the carbon material further includes a metal particle combined with the carbon material, and the metal particle comprising silver, and the metal particle has a diameter falling within a range from 2 nm to 2 mm, and occupies a percentage by weight of the carbon material below 20 wt %;
    the carbon material in the pharmaceutical composition contacting a bladder or related tissues of the bladder in an animal body;
    the water-containing carrier is selected from the group consisting of a buffer solution, the buffer solution containing an antibiotic medicament, the buffer solution containing cystitis medication, and the buffer solution containing both the antibiotic and the cystitis medication; and
    the pharmaceutical composition reducing symptoms of cystitis.

2. The pharmaceutical composition for treating urinary system disorders as recited in claim 1, wherein the water-containing carrier carries the carbon material, and the carried carbon material has a content of over 0.01 mg/ml per unit dose.

3. The pharmaceutical composition for treating urinary system disorders as recited in claim 2, wherein the carbon material carried in the water-containing carrier has a concentration per unit dose ranging from 0.1 mg/ml to 500 mg/ml.

4. The pharmaceutical composition for treating urinary system disorders as recited in claim 1, wherein the percentage by weight of the carbon content of the carbon material is over 80% by element weight.

5. The pharmaceutical composition for treating urinary system disorders as recited in claim 1, wherein the metal particle further occupies a percentage by weight of the carbon material below 5 wt %.

6. The pharmaceutical composition for treating urinary system disorders as recited in claim 1, wherein the carbon material has a structure and specific surface area (BET) falling within a range from 20 m$^2$/g to 4000 m$^2$/g.

7. The pharmaceutical composition for treating urinary system disorders as recited in claim 6, wherein the carbon material has a structure and specific surface area (BET) falling within a range from 200 m$^2$/g to 2000 m$^2$/g.

8. The pharmaceutical composition for treating urinary system disorders as recited in claim 1, comprising
    the carbon material having a diameter falling within a range from 20 nm to 2 mm.

9. A pharmaceutical composition for treating urinary system disorders, comprising a water-containing carrier carrying a carbon material having a carbon content over 60 percentage by weight (wt %), such that the water-containing carrier and the carbon material constitute a pharmaceutically acceptable water-containing carrier carrying the carbon material, and the carbon material includes a metal particle, and the metal particle occupies a percentage by weight of the water-containing carrier carrying the carbon material below 20 wt %, wherein the carbon material is one selected from the collection of carbon fiber, active carbon fiber, active carbon, nano-carbon tube, carbon nanocapsule, coke ball, carbon black, and a combination of the above, and the carbon material has a diameter falling within a range from 2 nm to 2 mm; thereby, the pharmaceutical composition of the water-containing carrier carrying the carbon material is capable of reducing symptoms of a cystitis by contacting the pharmaceutical composition containing the carbon material with a bladder or related tissues of the bladder in an animal body.

10. The pharmaceutical composition for treating urinary system disorders as recited in claim 9, wherein the carbon material includes a carbon content over 80 percentage by weight (wt %), and a fine granular metal particle selected from the collection of silver, platinum, palladium, gold, zinc and copper particles and a combination of the above, and the metal particle has a diameter falling within a range from 5 nm to 2 mm, and occupies a percentage by weight of the carbon material below 5 wt %.

11. The pharmaceutical composition for treating urinary system disorders as recited in claim 9, wherein the water-containing carrier carrying the carbon material falls within a range from 0.1 mg/ml to 500 mg/ml per unit dose.

12. The pharmaceutical composition for treating urinary system disorders as recited in claim 9, wherein the carbon material has a structure and specific surface area (BET) ranging from 200 m$^2$/g to 2000 m$^2$/g.

13. The pharmaceutical composition for treating urinary system disorders as recited in claim 9, wherein the water-containing carrier is selected from the group consisting of a buffer solution, the buffer solution containing an antibiotic medicament, the buffer solution containing cystitis medication, and the buffer solution containing both the antibiotic and the cystitis medication.

14. The pharmaceutical composition for treating urinary system disorders as recited in claim 13, wherein the antibiotic medicament is selected from the group consisting of trimethoprim-sulfame-thoxazole (TMP-SMX), trimethoprim (TMP), sulfame-thoxazole (SMX), fluoroquinolones, ciprofloxacin, ofloxacin, cephalexin, tetracycline and a combination of the above.

15. The pharmaceutical composition for treating urinary system disorders as recited in claim 13, wherein the bladder medication is a cystitis medication selected from the group consisting of dimethyl sulfoxide, clorpactin, heparin, hyaluronic acid (HA), adriamycin (ADM), chondroitin sulfate, sodium bicarbonate, silver nitrite, pentosan polysulfate sodium, cromolyn sodium, pencillin, nitrofurazone, gentamicin, mild silver protein and a combination of the above.

* * * * *